(12) United States Patent
Sasaki

(10) Patent No.: US 9,720,056 B2
(45) Date of Patent: *Aug. 1, 2017

(54) MAGNETIC SENSOR, MAGNETIC HEAD, AND BIOMAGNETIC SENSOR

(71) Applicant: TDK CORPORATION, Tokyo (JP)

(72) Inventor: Tomoyuki Sasaki, Tokyo (JP)

(73) Assignee: TDK CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/941,062

(22) Filed: Nov. 13, 2015

(65) Prior Publication Data

US 2016/0154071 A1   Jun. 2, 2016

(30) Foreign Application Priority Data

Dec. 1, 2014   (JP) .................. 2014-243063

(51) Int. Cl.
   *G11B 5/39*   (2006.01)
   *G01R 33/09*   (2006.01)
   *A61B 5/05*   (2006.01)
   *H01L 43/08*   (2006.01)

(52) U.S. Cl.
   CPC .............. *G01R 33/093* (2013.01); *A61B 5/05* (2013.01); *G11B 5/3906* (2013.01); *G11B 5/398* (2013.01); *G11B 5/3929* (2013.01); *G11B 5/3945* (2013.01); *H01L 43/08* (2013.01); *A61B 2562/0223* (2013.01)

(58) Field of Classification Search
   CPC .... G11B 5/3906; G11B 5/3929; G11B 5/3945
   USPC ...................... 360/316, 324.1, 324.12, 324.2
   See application file for complete search history.

(56) References Cited

U.S. PATENT DOCUMENTS

| | | | |
|---|---|---|---|
| 7,209,328 B2 | 4/2007 | Ito et al. | |
| 7,969,692 B2 | 6/2011 | Takahashi | |
| 8,085,513 B2 | 12/2011 | Sasaki | |
| 8,339,750 B2* | 12/2012 | Sasaki | G01R 33/098 360/319 |
| 8,426,929 B2 | 4/2013 | Sasaki et al. | |
| 8,711,528 B1* | 4/2014 | Xiao | G11B 5/3909 360/122 |
| 8,766,733 B2* | 7/2014 | Cyrille | H03B 15/006 331/94.1 |
| 9,123,361 B1* | 9/2015 | Kief | G11B 5/265 |
| 2005/0002128 A1 | 1/2005 | Ito et al. | |

(Continued)

FOREIGN PATENT DOCUMENTS

| | | |
|---|---|---|
| JP | 2007299467 A | 11/2007 |
| JP | 4029772 B2 | 1/2008 |

(Continued)

OTHER PUBLICATIONS

Sasaki et al., "Electrical Spin Injection into Silicon Using MgO Tunnel Barrier," Applied Physics Express 2, 2009, pp. 1-3.

*Primary Examiner* — Jefferson Evans
(74) *Attorney, Agent, or Firm* — Oliff PLC

(57) ABSTRACT

A magnetic sensor includes a channel layer, a magnetization free layer placed on a first section of the channel layer, and a magnetization-fixed layer placed on a second section of the channel layer. The areal resistance of the interface between the channel layer and the magnetization free layer is lower than the areal resistance of the interface between the channel layer and the magnetization-fixed layer.

11 Claims, 6 Drawing Sheets

(56) References Cited

U.S. PATENT DOCUMENTS

| | | | | |
|---|---|---|---|---|
| 2006/0262458 A1* | 11/2006 | Carey | ............... | G01R 33/093 360/324.2 |
| 2007/0253116 A1 | 11/2007 | Takahashi | | |
| 2010/0119875 A1 | 5/2010 | Sasaki | | |
| 2010/0314702 A1* | 12/2010 | Sasaki | ............... | G11C 11/16 257/421 |
| 2011/0254585 A1* | 10/2011 | Apalkov | ............... | H03K 19/16 326/37 |
| 2012/0211848 A1* | 8/2012 | Sasaki | ............... | H01L 43/08 257/422 |
| 2014/0292318 A1* | 10/2014 | Wang | ............... | B82Y 25/00 324/228 |
| 2015/0035524 A1* | 2/2015 | Sasaki | ............... | G01R 33/093 324/244 |
| 2016/0293740 A1* | 10/2016 | Sasaki | ............... | G01R 33/098 |
| 2017/0092302 A1* | 3/2017 | Deen | ............... | G11B 5/3903 |
| 2017/0092305 A1* | 3/2017 | Deen | ............... | G11B 5/3912 |

FOREIGN PATENT DOCUMENTS

| | | |
|---|---|---|
| JP | 2010113788 A | 5/2010 |
| JP | 2012174323 A | 9/2012 |
| JP | 2015046212 A | 3/2015 |

* cited by examiner

MAGNETIC SENSOR, MAGNETIC HEAD, AND BIOMAGNETIC SENSOR

BACKGROUND OF THE INVENTION

1. Field of the Invention

The present invention relates to a magnetic sensor, a magnetic head, and a biomagnetic sensor.

2. Description of the Related Art

Magnetoresistive sensors are known as magnetic sensors for use in thin-film magnetic recording/reproducing heads and the like. In general, a magnetoresistive sensor applies a current between a magnetization-fixed layer and a magnetization free layer and therefore provides a high output. However, the magnetoresistive sensor receives a signal, caused by the motion of a domain wall due to current-induced spin torque or the like, unnecessary for magnetic sensors.

Spin accumulation (SA) magnetic sensors each including a magnetization free layer and magnetization-fixed layer formed on the same horizontal surface (a channel layer for accumulating spins) are known (refer to, for example, Japanese Unexamined Patent Application Publication No. 2007-299467 and Japanese Patent No. 4029772). For example, when a thin-film magnetic recording/reproducing head includes a spin accumulation magnetic sensor, no current needs to be applied to a magnetization free layer detecting the external magnetic field of a magnetic recording medium or the like. That is, the spin accumulation magnetic sensor can detect magnetic condition in the form of an output voltage using a spin current only.

In order to put spin accumulation magnetic sensors to practical use, some problems need to be solved. One of the problems is noise. In the case of, for example, a magnetoresistive magnetic sensor, a current is applied to a multilayer film detecting a voltage and therefore the resistance of the multilayer film can be a cause of Johnson noise or the like. In the case of a spin accumulation magnetic sensor, a current is applied between a channel layer and a multilayer film for applying spins to the channel layer, whereby spins are injected into the channel layer. The current applied therebetween is a cause of noise. The noise of a current acts as the noise of a spin current and is detected together with output; hence, a high signal-to-noise (S/N) ratio is not obtained. A solution to this problem is to increase the cross-sectional area of a multilayer film in contact with a channel layer as disclosed in, for example, Japanese Unexamined Patent Application Publication No. 2010-113788. However, any solution to noise due to the detection side of a spin current is not described therein.

In the case of a spin accumulation magnetic head, a magnetization free layer detecting an external magnetic field needs to be smaller than a magnetization-fixed layer in order to enhance spatial resolution with respect to the external magnetic field and therefore the magnetization free layer generally has higher interfacial resistance. When the magnetization free layer, which is placed on a channel layer, and the magnetization-fixed layer have the same multilayer structure, the areal resistance of the interface between the channel layer and the magnetization free layer is equal to the areal resistance of the interface between the channel layer and the magnetization-fixed layer. Thus, in the case where the magnetization free layer is prepared so as to be smaller than the magnetization-fixed layer, the resistance of the interface between the channel layer and the magnetization free layer is higher than the resistance of the interface between the channel layer and the magnetization-fixed layer. This applies to the case where the magnetization free layer is used as an injection source of a spin current and the case where the magnetization free layer is used as an electrode for detecting a spin current. When the resistance of the interface between the magnetization free layer and the channel layer is high, there is a problem in that no high S/N ratio is obtained because Johnson noise increases in proportion to circuit resistance.

SUMMARY OF THE INVENTION

The present invention has been made in view of the above circumstances. It is an object of the present invention to provide a magnetic sensor providing a high S/N ratio, a magnetic head including the magnetic sensor, and a biomagnetic sensor including the magnetic sensor.

In order to solve the above problems, a magnetic sensor according to the present invention includes a channel layer, a magnetization free layer placed on a first section of the channel layer, and a magnetization-fixed layer placed on a second section of the channel layer. The areal resistance of the interface between the channel layer and the magnetization free layer is lower than the areal resistance of the interface between the channel layer and the magnetization-fixed layer.

Since the areal resistance of the interface between the channel layer and the magnetization free layer is lower than the areal resistance of the interface between the channel layer and the magnetization-fixed layer, the resistance of the interface between the channel layer and the magnetization free layer is low as compared to the case where the areal resistance of the interface between the channel layer and the magnetization free layer is equal to the areal resistance of the interface between the channel layer and the magnetization-fixed layer; hence, detection noise can be reduced. Furthermore, the resistance of the interface between the channel layer and the magnetization-fixed layer is high as compared to the case where the areal resistance of the interface between the channel layer and the magnetization free layer is equal to the areal resistance of the interface between the channel layer and the magnetization-fixed layer; hence, a high output is obtained. The magnetic sensor provides a high S/N ratio due to either or both of these effects.

The term "areal resistance (RA)" as used herein is expressed as the product of the resistance ($\Omega$) and the area ($\mu m^2$) of a cross section perpendicular to the direction of a current. That is, the resistance is obtained by dividing the areal resistance by the cross-sectional area.

In the present invention, the resistance of an interface refers to the resistance of the interface between the channel layer and a ferromagnetic sub-layer in the magnetization free layer or the magnetization-fixed layer and includes the resistance due to either or both of a tunnel barrier layer or Schottky barrier placed between the channel layer and the ferromagnetic sub-layer.

The areal resistance of the interface between the channel layer and the magnetization free layer is given by the product of the above-mentioned interface resistance and the area of the interface between the channel layer and the magnetization free layer. When a tunnel barrier layer is placed between the channel layer and the ferromagnetic sub-layer in the magnetization free layer, the areal resistance of the interface between the channel layer and the magnetization free layer is given by the product of the above-mentioned interface resistance and the area of the interface between the tunnel barrier layer and the ferromagnetic sub-layer in the magnetization free layer. Likewise, the areal resistance of the interface between the channel layer and the magnetization-fixed layer is given by the product of the above-mentioned interface resistance and the area of the interface between the channel layer and the magnetization-fixed layer. When a tunnel barrier layer is placed between the channel layer and the ferromagnetic sub-layer in the magnetization-fixed layer, the areal resistance of the interface between the channel layer and the magnetization free layer is given by the product of the above-mentioned interface resistance and the area of the interface between the tunnel barrier layer and the ferromagnetic sub-layer in the magnetization-fixed layer.

It is preferred that the magnetization free layer includes a first ferromagnetic sub-layer and a first tunnel barrier sub-layer placed between the first ferromagnetic sub-layer and the channel layer, the magnetization-fixed layer includes a second ferromagnetic sub-layer and a second tunnel barrier sub-layer placed between the second ferromagnetic sub-layer and the channel layer, and the thickness of the first tunnel barrier sub-layer is less than the thickness of the second tunnel barrier sub-layer.

Varying the thickness of the first tunnel barrier sub-layer and the second tunnel barrier sub-layer allows the areal resistance of the interface between the channel layer and the magnetization free layer to be readily adjusted below the areal resistance of the interface between the channel layer and the magnetization-fixed layer. That is, the magnetic sensor can be prepared so as to have industrially stable properties.

The thickness d1 of the first section of the channel layer, the thickness of the channel layer under the magnetization free layer is preferably less than the thickness d2 of the second section of the channel layer, that is, the thickness of the channel layer under the magnetization-fixed layer. In this case, spatial resolution with respect to an external magnetic field is high, which is preferred.

The thickness d2 of the second section of the channel layer is preferably less than the thickness d1 of the first section of the channel layer. In this case, an obtained output is high as compared to the case where the thickness d1 of the first section of the channel layer is less than the thickness d2 of the second section of the channel layer.

A magnetic head according to the present invention may include a reading head section including the magnetic sensor and a recording head section for writing. In this case, the magnetization free layer, which detects external magnetic flux, is preferably covered with an upper, a lower, a left, and a right magnetic shield. The read gap between the upper and lower magnetic shields corresponds to spatial resolution to detect external magnetic flux. In the read gap, there are at least three layers: an insulating layer for electrically and magnetically isolating a portion of the channel layer that conducts spins from the lower magnetic shield, the channel layer, and the magnetization free layer are present. When the thickness d1 of the first section of the channel layer, that is, the thickness of the channel layer under the magnetization free layer is less than the thickness d2 of the second section of the channel layer, that is, the thickness of the channel layer under the magnetization-fixed layer, the read gap is narrow and therefore spatial resolution is high.

A biomagnetic sensor according to the present invention may include a plurality of magnetic sensors having the same configuration as that of the magnetic sensor. In general, as the distance between the magnetization-fixed layer and the magnetization free layer is smaller, the biomagnetic sensor provides a higher output. The biomagnetic sensor includes the magnetic sensors and therefore can detect where fine magnetic particles are located, the number of the fine magnetic particles, and the size of the fine magnetic particles.

The present invention can provide a magnetic sensor providing a high S/N ratio, a magnetic head including the magnetic sensor, and a biomagnetic sensor including the magnetic sensor.

DESCRIPTION OF THE PREFERRED EMBODIMENTS

Figure 1:
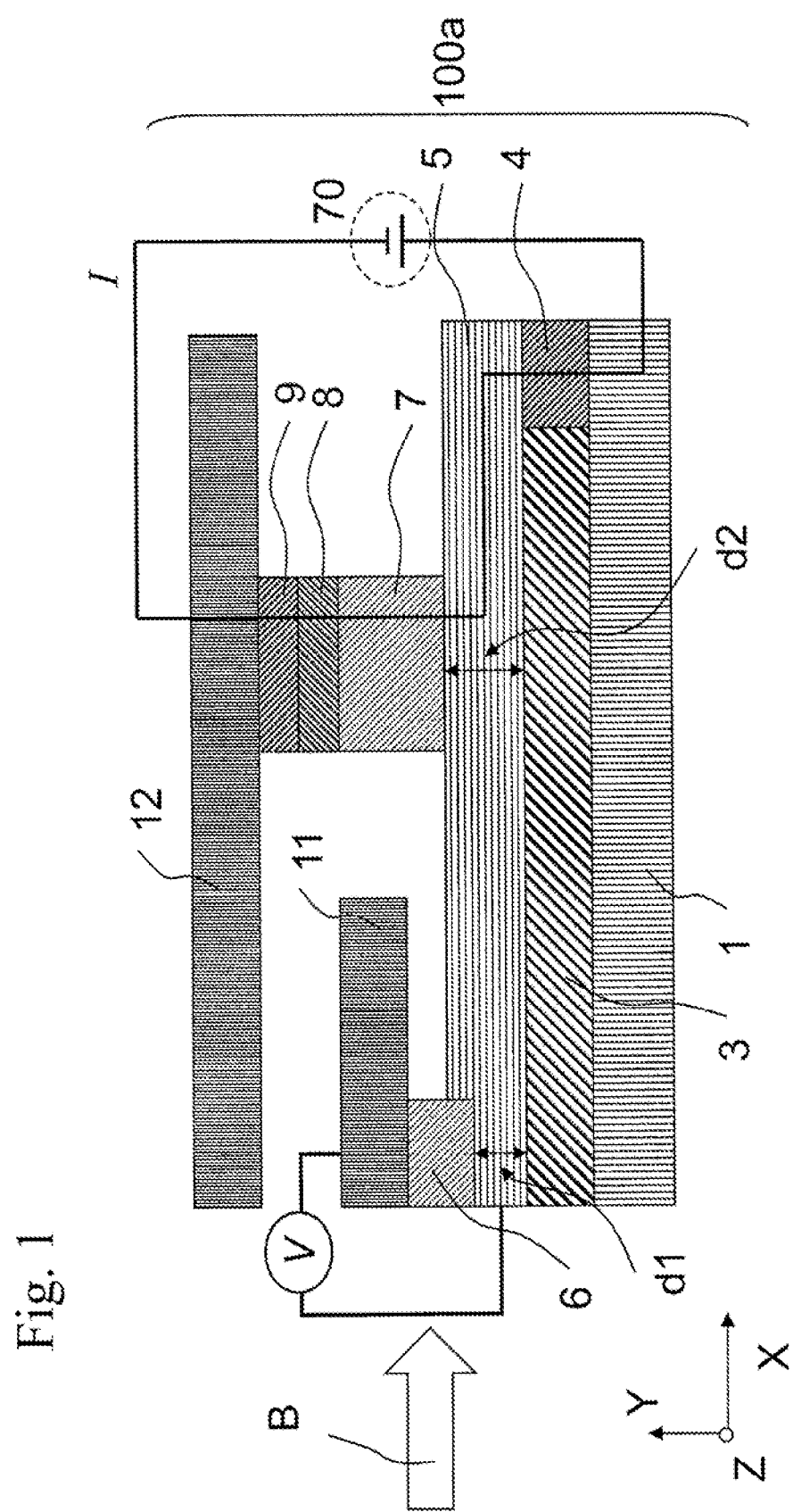
FIG. 1 is a schematic sectional view of a magnetic sensor according to a first embodiment of the present invention.

Embodiments of the present invention will now be described in detail with reference to the attached drawings. In the description of the drawings, the same components are designated by the same reference numerals and will not be described redundantly.

First Embodiment

A magnetic sensor 100a according to a first embodiment of the present invention is described below with reference to FIG. 1.

The magnetic sensor 100a is placed on a substrate and is covered by a non-magnetic insulating layer made of alumina or the like. As shown in FIG. 1, the magnetic sensor 100a includes a channel layer 5 which accumulates and transports the spins of electrons and which includes a first section and a second section different from the first section, a magnetization free layer 6 placed on the first section of the channel layer 5, and a magnetization-fixed layer 7 placed on the second section of the channel layer 5. The magnetic sensor 100a further includes a lower magnetic shield layer 1, an upper first magnetic shield layer 11 facing the lower magnetic shield layer 1 with the channel layer 5 therebetween, an upper second magnetic shield layer 12 facing the lower magnetic shield layer 1 with the channel layer 5 therebetween, a first insulating layer 3 placed between the lower magnetic shield layer 1 and the channel layer 5, a first electrode 4 placed between the lower magnetic shield layer 1 and the channel layer 5, an antiferromagnetic layer 8 placed on the magnetization-fixed layer 7, and a second electrode 9 placed on the antiferromagnetic layer 8.

The thickness d1 of the first section of the channel layer 5 is less than the thickness d2 of the second section the channel layer 5. The difference between the thickness d2 of the second section of the channel layer 5 and the thickness d1 of the first section of the channel layer 5 has no significant influence on the effect of reducing noise. In particular, in the case of use as a thin-film magnetic reproducing head 100A, the thickness d1 of the first section of the channel layer 5 is preferably less than the thickness d2 of the second section of the channel layer 5 because spatial resolution with respect to external magnetic flux becomes high.

In the case where the magnetization free layer 6 and the magnetization-fixed layer 7 are prepared so as to have different multilayer structures, the magnetization free layer 6 and the magnetization-fixed layer 7 are prepared by separate thin-film processes. For example, in the case where the magnetization free layer 6 is prepared after the magnetization-fixed layer is prepared, a surface of the channel layer 5 that is in contact with the magnetization free layer 6 is contaminated by a process for preparing the magnetization-fixed layer 7. Thus, before the magnetization free layer 6 is prepared, a surface of the channel layer 5 is preferably cleaned by, for example, chemical treatment or ion milling. The surface cleanliness of the channel layer 5 is improved by this process. Furthermore, as shown in FIG. 1, the channel layer 5 under the magnetization free layer 6 is etched by this process and therefore the thickness d1 of the first section of the channel layer 5 becomes less than the thickness d2 of the second section of the channel layer 5.

Figure 2:
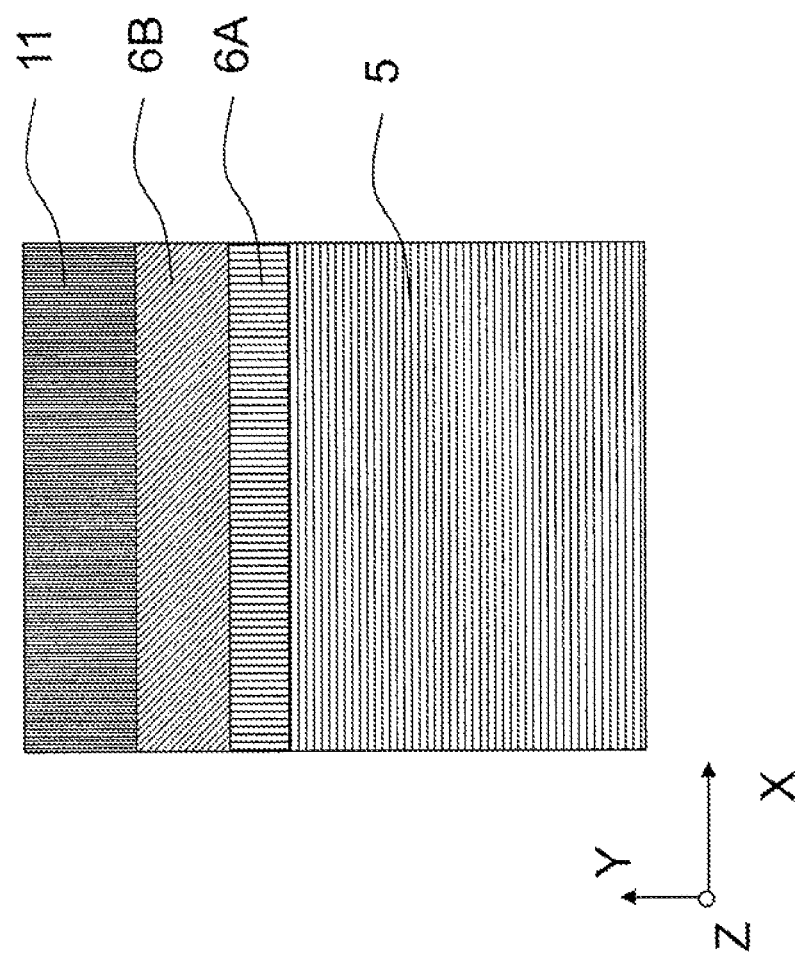
FIG. 2 is a detailed sectional view of a magnetization free layer.

As shown in FIG. 2 in an enlarged manner, the magnetization free layer 6 is composed of a first ferromagnetic sub-layer 6B and a first tunnel barrier sub-layer 6A placed between the channel layer 5 and the first ferromagnetic sub-layer 6B. The first ferromagnetic sub-layer 6B is one for detecting an external magnetic field to acutely detect the change in magnetization direction of a magnetic recording medium or the like. The magnetization free layer 6 is placed on the upper surface of the channel layer 5 and is located on the side where magnetic flux which is an object detected by the channel layer 5 enters. The first tunnel barrier sub-layer 6A, which is shown in FIG. 2, may be omitted. In this case, the areal resistance of the interface between the first ferromagnetic sub-layer 6B and the channel layer 5 may be adjusted in such a manner that the channel layer 5 is surface-modified with Ar plasma.

The first tunnel barrier sub-layer 6A is preferably made of an insulating material. Examples of the insulating material include MgO, $Al_2O_3$, $MgAl_2O_4$, $TaO_x$, and $SiO_x$. The first tunnel barrier sub-layer 6A is preferably crystalline. In this case, when a spin-polarized current passes through the first tunnel barrier sub-layer 6A, spin polarizability is increased by a spin filter effect; hence, high output characteristics can be obtained. The first tunnel barrier sub-layer 6A may be replaced with a Schottky barrier formed in the channel layer 5. When the channel layer 5 is made of a semiconductor material, the Schottky barrier is formed between metals in a ferromagnetic layer. Alternatively, the first tunnel barrier sub-layer 6A may have both the function of an insulating film and the function of the Schottky barrier.

A ferromagnetic material, particularly a soft magnetic material, is used as a material for forming the first ferromagnetic sub-layer 6B. The following metal or alloy is cited: for example, a metal selected from the group consisting of Co, Fe, and Ni; an alloy containing one or more selected from the group consisting of Cr, Mn, Co, Fe, and Ni; or an alloy containing one or more selected from the group consisting of Cr, Mn, Co, Fe, and Ni and at least one selected from the group consisting of B, C, and N. In particular, Co—Fe, Co—Fe—B, or Ni—Fe is cited.

Figure 3:
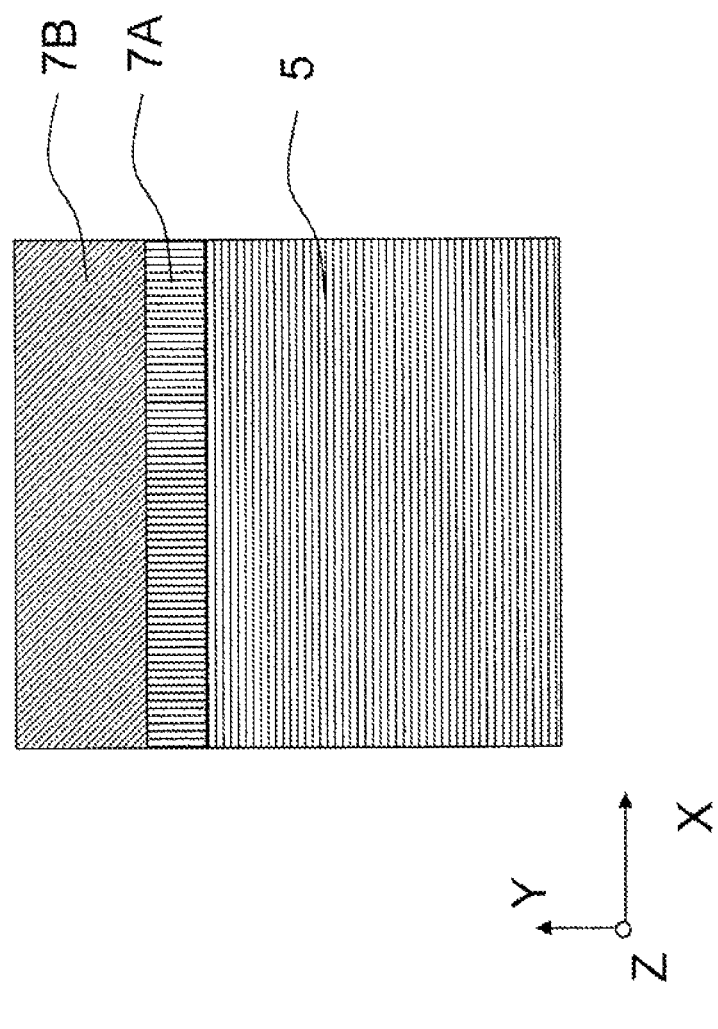
FIG. 3 is a detailed sectional view of a magnetization-fixed layer.

As shown in FIG. 3 in an enlarged manner, the magnetization-fixed layer 7 is composed of a second ferromagnetic sub-layer 7B and a second tunnel barrier sub-layer 7A placed between the channel layer 5 and the second ferromagnetic sub-layer 7B. The second ferromagnetic sub-layer 7B is one for injecting electrons having a predetermined spin into the channel layer 5. The magnetization-fixed layer 7 is placed on the upper surface of the channel layer 5 and is located on the side opposite to the side where magnetic flux which is an object detected by the channel layer 5 enters. The second tunnel barrier sub-layer 7A, which is shown in FIG. 3, may be omitted. In this case, the areal resistance of the interface between the second ferromagnetic sub-layer 7B and the channel layer 5 may be adjusted in such a manner that the channel layer 5 is surface-modified with Ar plasma.

The second tunnel barrier sub-layer 7A is preferably made of an insulating material. Examples of the insulating material include MgO, $Al_2O_3$, $MgAl_2O_4$, $TaO_x$, and $SiO_x$. The second tunnel barrier sub-layer 7A is preferably crystalline. In this case, when a spin-polarized current passes through the second tunnel barrier sub-layer 7A, spin polarizability is increased by a spin filter effect; hence, high output characteristics can be obtained. The second tunnel barrier sub-layer 7A may be replaced with a Schottky barrier formed in the channel layer 5. When the channel layer 5 is made of a semiconductor material, a Schottky barrier is formed between metals in a ferromagnetic layer. Alternatively, the second tunnel barrier sub-layer 7A may have both the function of an insulating film and the function of the Schottky barrier.

The thickness of the first tunnel barrier sub-layer 6A is preferably less than the thickness of the second tunnel barrier sub-layer 7A. This allows the areal resistance of the interface between the channel layer 5 and the magnetization free layer 6 to be readily adjusted below the areal resistance of the interface between the channel layer 5 and the magnetization-fixed layer 7. The first tunnel barrier sub-layer 6A may be omitted and the second tunnel barrier sub-layer 7A may be present.

A ferromagnetic metal material with high spin polarizability can be used to form the second ferromagnetic sub-layer 7B. The following metal or alloy is cited: for example, a metal selected from the group consisting of Co, Fe, and Ni; an alloy containing one or more selected from the group consisting of Cr, Mn, Co, Fe, and Ni; or an alloy containing one or more selected from the group consisting of Cr, Mn, Co, Fe, and Ni and at least one selected from the group consisting of B, C, and N. In particular, Co—Fe or Co—Fe—B is cited. Furthermore, in order to obtain a high output, a Heusler alloy such as $Co_2FeSi$ is preferably used. Heusler alloys include intermetallic compounds having the chemical composition $X_2YZ$, where X is a Co-, Fe-, Ni-, or Cu-group transition metal element or a noble metal on the periodic table; Y is a Mn-, V-, Cr-, or Ti-group transition metal or can take the element species of X; and Z is a typical element of Group III to Group V. For example, $Co_2FeSi$, $Co_2MoSi$, and the like are cited.

The coercive force of the second ferromagnetic sub-layer 7B is greater than the coercive force of the first ferromagnetic sub-layer 6B. The magnetization of the second ferromagnetic sub-layer 7B is preferably fixed by at least one of a magnetization-fixing method using the antiferromagnetic layer 8 and a magnetization-fixing method making use of the shape magnetic anisotropy of the second ferromagnetic sub-layer 7B. This allows the magnetization direction of the second ferromagnetic sub-layer 7B to be unlikely to respond to an external magnetic field.

In the case of using the magnetization-fixing method using the antiferromagnetic layer 8 to fix the magnetization of the second ferromagnetic sub-layer 7B, the antiferromagnetic layer 8 is placed on the second ferromagnetic sub-layer 7B as shown in FIG. 1. The exchange coupling of the antiferromagnetic layer 8 with the second ferromagnetic sub-layer 7B enables the magnetization direction of the second ferromagnetic sub-layer 7B to be fixed (unidirectional anisotropy to be imparted to the second ferromagnetic sub-layer 7B). This allows the second ferromagnetic sub-layer 7B to have high coercive force in one direction as compared to the case of the absence of the antiferromagnetic layer 8. Thus, a material used to form the antiferromagnetic layer 8 is selected in accordance with a material used to form the second ferromagnetic sub-layer 7B. An example of the material used to form the antiferromagnetic layer 8 is an alloy which contains Mn and which exhibits antiferromagnetic properties, particularly an alloy containing Mn and at least one selected from the group consisting of Pt, Ir, and Fe. In particular, for example, Ir—Mn or Pt—Mn is cited.

In the case of using a method allowing the second ferromagnetic sub-layer 7B to have shape magnetic anisotropy to fix the magnetization of the second ferromagnetic sub-layer 7B, the antiferromagnetic layer 8 may be omitted. The magnetization of the second ferromagnetic sub-layer 7B may be fixed using both the antiferromagnetic layer 8 and shape magnetic anisotropy.

As a material for forming the channel layer 5, a non-ferromagnetic conductive material is cited and a material having a large spin diffusion length and relatively low conductivity is preferably selected. The material for forming the channel layer 5 is, for example, a metal material containing one or more selected from the group consisting of Ag, Cu, Al, and Mg. In particular, Ag, Cu, and MgB$_2$ are preferred. These metal materials have a relatively large spin diffusion length and therefore a high output can be obtained with low noise.

The material for forming the channel layer 5 is preferably a semiconductor material such as Si, SiGe, Ge, ZnO, GaAs, graphene, or diamond. The semiconductor material has a very large spin diffusion length and therefore a high output can be obtained.

The first insulating layer 3 prevents the spins of electrons accumulated in the channel layer 5 from flowing to the lower magnetic shield layer 1 side. The first insulating layer 3 is placed between the channel layer 5 and the lower magnetic shield layer 1. From the viewpoint of efficiently accumulating spins, the first insulating layer 3 is preferably placed on the lower surface of the channel layer 5 so as to extend from the magnetization-fixed layer 7 side to the magnetization free layer 6 side. For example, SiO$_2$ is cited as a material for forming the first insulating layer 3.

The first electrode 4 is an electrode for applying a detection current to the magnetization-fixed layer 7. The first electrode 4 is placed on the lower surface of the channel layer 5, is located opposite to the side where an external magnetic field enters, and abuts on the first insulating layer 3. Referring to FIG. 1, the channel layer 5 is electrically connected to the lower magnetic shield layer 1 through the first electrode 4. Thus, the lower magnetic shield layer 1, which is placed under the first electrode 4, can be used as an electrode for applying a detection current I to the magnetization-fixed layer 7. For example, a metal material such as Cu or Ta is used to form the first electrode 4.

The second electrode 9 is an electrode for electrically connecting the upper second magnetic shield layer 12 to the antiferromagnetic layer 8 by applying a current to the magnetization-fixed layer 7 using the upper second magnetic shield layer 12 as an electrode. The second electrode 9 has the effect of suppressing the diffusion of atoms between the upper second magnetic shield layer 12 and the antiferromagnetic layer 8 or the magnetization-fixed layer 7. For example, a metal material such as Cu or Ta is used to form the second electrode 9.

In the magnetic sensor 100a, a current is applied between the magnetization-fixed layer 7 (second ferromagnetic sub-layer 7B) and the channel layer 5 and the voltage between the magnetization free layer 6 (first ferromagnetic sub-layer 6B) and the channel layer 5 is detected. Since a current is applied between the magnetization-fixed layer 7 (second ferromagnetic sub-layer 7B) and the channel layer 5, spins are injected into the channel layer 5 from the magnetization-fixed layer 7.

The resistance of the interface between the channel layer 5 and the magnetization-fixed layer 7 is preferably higher than the spin resistance. In this case, the effect that the spins injected into the channel layer 5 from the magnetization-fixed layer 7 return from the channel layer 5 to the magnetization-fixed layer 7 can be suppressed and therefore a reduction in output due to this effect can be suppressed. No spin injection occurs between the channel layer 5 and the magnetization free layer 6 and therefore the resistance of the interface between the channel layer 5 and the magnetization free layer 6 need not be high. In the magnetic sensor 100a, noise in a detection circuit can be reduced in such a manner that the resistance of the interface between the channel layer 5 and the magnetization free layer 6 is reduced such that the areal resistance of the interface between the channel layer 5 and the magnetization free layer 6 is lower than the areal resistance of the interface between the channel layer 5 and the magnetization-fixed layer 7. The magnetic sensor 100a provides a high output as compared to the case where the areal resistance of the interface between the magnetization free layer 6 and the channel layer 5 is equal to the areal resistance of the interface between the magnetization-fixed layer 7 and the channel layer 5, because the resistance of the interface between the magnetization-fixed layer 7 and the channel layer 5 is high. Thus, when the areal resistance of the interface between the channel layer 5 and the magnetization free layer 6 is lower than the areal resistance of the interface between the channel layer 5 and the magnetization-fixed layer 7, a high S/N ratio can be obtained by either or both of the effect of reducing noise and the effect of providing a high output.

The spin resistance is defined by the following formula:

$$\frac{P^2 \lambda_N}{\sigma A}$$

where P is the injection/detection efficiency of spins, $\lambda_N$ is the spin diffusion length, $\sigma$ is the electrical conductivity of a channel layer, and A is the cross-sectional area of the channel layer. The definition of the spin resistance by the formula is limited to the case where the channel layer is such a conductor that can conduct a current. When the channel layer is made of a high-resistance material typified by an insulator, the spin resistance is not defined by the formula.

The operation of the magnetic sensor 100a is described below with reference to FIG. 1. In order to apply a detection current to the magnetization-fixed layer 7, the lower magnetic shield layer 1 and the upper second magnetic shield layer 12 are electrically connected to a current source 70. In order to measure the voltage generated between the channel layer 5 and the magnetization free layer 6 (first ferromagnetic sub-layer 6B), the channel layer 5 and the upper first magnetic shield layer 11 are electrically connected to a voltage-measuring system 80. In the case where the upper first magnetic shield layer 11 is spaced apart from the first ferromagnetic sub-layer 6B and is insulated from the first ferromagnetic sub-layer 6B, the channel layer 5 and the first ferromagnetic sub-layer 6B may be electrically connected to the voltage-measuring system 80.

A detection current I is applied to the magnetization-fixed layer 7 of the magnetic sensor 100a. For example, a detection current I is applied from the current source 70 to the lower magnetic shield layer 1, the first electrode 4, the channel layer 5, the magnetization-fixed layer 7, the antiferromagnetic layer 8, the second electrode 9, and the upper second magnetic shield layer 12 in that order as shown in FIG. 1.

When a detection current I is applied from the channel layer 5 to the second ferromagnetic sub-layer 7B, which is ferromagnetic, electrons each having a spin corresponding to the magnetization direction of the second ferromagnetic sub-layer 7B are injected into the channel layer 5 from the second ferromagnetic sub-layer 7B (spin injection). The spins are accumulated in the channel layer 5 (spin accumulation) and then diffuse from the magnetization-fixed layer 7 side toward the magnetization free layer 6 side. In the case of applying a current in the opposite direction, electrons having spins are extracted from the channel layer 5 to the second ferromagnetic sub-layer 7B. In this case, spins are accumulated in the channel layer 5 alike.

A voltage output is generated between the first ferromagnetic sub-layer 6B and the channel layer 5 depending on the relative angle between the magnetization direction of the first ferromagnetic sub-layer 6B, which is varied in magnetization direction by a magnetic field from outside, and the magnetization direction of the second ferromagnetic sub-layer 7B. In this embodiment, the voltage generated between the channel layer 5 and the upper first magnetic shield layer 11 is detected. Therefore, the magnetic sensor 100a can be used as an external magnetic field sensor. The magnetic sensor 100a is evaluated by a method called a non-local measurement method and can be measured by, for example, a method described in Applied Physics Express 2, 053003 (2009).

In this embodiment, the first tunnel barrier sub-layer 6A is located between the channel layer 5 and the first ferromagnetic sub-layer 6B and the second tunnel barrier sub-layer 7A is located between the channel layer 5 and the second ferromagnetic sub-layer 7B as described above. One or both of the first tunnel barrier sub-layer 6A and the second tunnel barrier sub-layer 7A, which are tunnel barriers, may be replaced with Schottky barriers. Alternatively, both a tunnel barrier layer and a Schottky barrier may be placed between the channel layer 5 and the first ferromagnetic sub-layer 6B or between the channel layer 5 and the second ferromagnetic sub-layer 7B. The magnetization free layer 6 need not include the first tunnel barrier sub-layer 6A and the channel layer 5 may be in contact with the first ferromagnetic sub-layer 6B. The magnetization-fixed layer 7 need not include the second tunnel barrier sub-layer 7A and the channel layer 5 may be in contact with the second ferromagnetic sub-layer 7B. In this case, a high S/N ratio is obtained in such a manner that the areal resistance of the interface between the channel layer 5 and the magnetization free layer 6 is adjusted below the areal resistance of the interface between the channel layer 5 and the magnetization-fixed layer 7.

In the case where a tunnel barrier layer and a Schottky barrier are provided between the channel layer 5 and the first ferromagnetic sub-layer 6B and a tunnel barrier layer and a Schottky barrier are provided between the channel layer 5 and the second ferromagnetic sub-layer 7B, the areal resistance of the interface between the channel layer 5 and the magnetization free layer 6 can be adjusted below the areal resistance of the interface between the channel layer 5 and the magnetization-fixed layer 7 in such a manner that, for example, the thicknesses of these barriers are allowed to differ between the magnetization free layer 6 and the magnetization-fixed layer 7. When the channel layer 5 and the first ferromagnetic sub-layer 6B in contact with each other and the channel layer 5 and the second ferromagnetic sub-layer 7B are in contact with each other, the areal resistance of the interface between the channel layer 5 and the magnetization free layer 6 can be adjusted below the areal resistance of the interface between the channel layer 5 and the magnetization-fixed layer 7 in such a manner that, for example, the surface condition of the channel layer 5 before the first ferromagnetic sub-layer 6B and the second ferromagnetic sub-layer 7B are formed is varied between the first ferromagnetic sub-layer 6B and the second ferromagnetic sub-layer 7B.

Second Embodiment

A magnetic head 100A according to a second embodiment of the present invention is described below. After the magnetic sensor 100a according to the first embodiment is prepared, a writing section is formed in the magnetic head 100A. The magnetic sensor 100a according to the first embodiment functions as a reading section in the magnetic head 100A.

Figure 5:
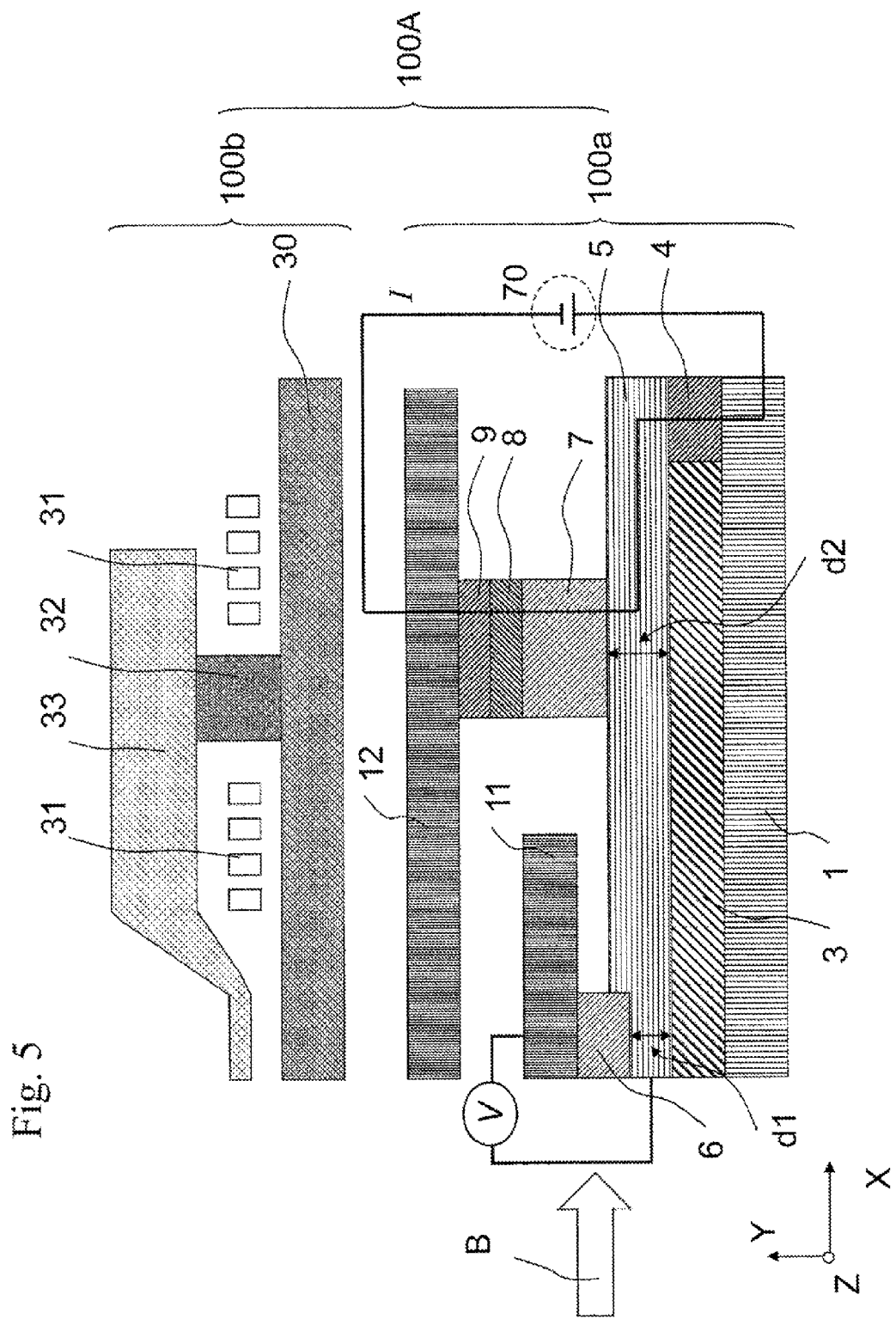
FIG. 5 is a schematic view of a magnetic head including the magnetic sensor shown in FIG. 1.

FIG. 5 is a schematic view of the magnetic head 100A. The magnetic head 100A includes the magnetic sensor 100a and a recording head section 100b for writing. In the magnetic head 100A, the magnetic sensor 100a is used in a reading head section. The recording head section 100b includes a return yoke 30, a contact section 32 placed on the return yoke 30, and a main magnetic pole 33 placed above the return yoke 30. The return yoke 30, the contact section 32, and the main magnetic pole 33 form a magnetic flux path. A thin-film coil 31 is placed so as to surround the contact section 32. When a recording current is applied to the thin-film coil 31, magnetic flux is expelled from the tip of the main magnetic pole 33, whereby information can be recorded on a recording layer of a magnetic recording medium such as a hard disk. As described above, the magnetic head 100A can detect magnetic flux from a micro-region of a recording medium or the like and can be provided using a magnetic sensor according to the present invention.

In this embodiment, a magnetization free layer detecting external magnetic flux is covered by magnetic shields and the thickness d1 of a first section of a channel layer, that is, the thickness of the channel layer under a magnetization free layer is less than the thickness d2 of a second section of the channel layer, that is, the thickness of the channel layer under a magnetization-fixed layer; hence, the read gap between the upper and lower magnetic shields is narrow and therefore spatial resolution is high.

Third Embodiment

Figure 6:
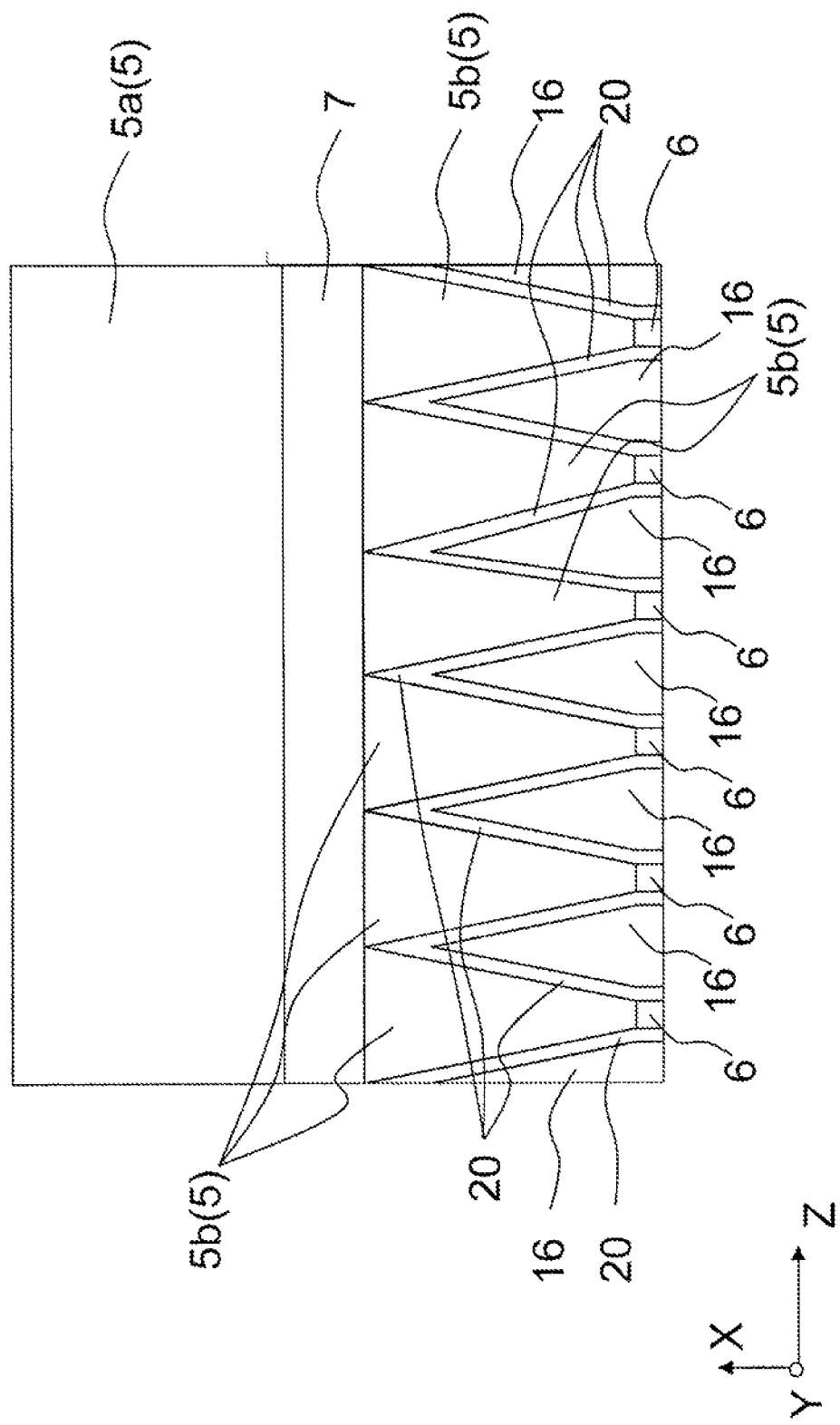
FIG. 6 is a schematic view of a biomagnetic sensor including a plurality of magnetic sensors.

FIG. 6 shows a biomagnetic sensor according to a third embodiment of the present invention. The biomagnetic sensor includes a plurality of biomagnetic sensors having the same configuration as that of the magnetic sensor 100a according to the first embodiment. As shown in FIG. 6, the biomagnetic sensor has a structure in which inter-element insulating layers 20 are arranged such that a spin current in each element does not flow into other elements.

When a current is applied between a magnetization-fixed layer 7 and channel layers 5, spins are injected into the channel layers 5. The spins injected into the channel layers 5 are transported to first ferromagnetic sub-layers 6B of magnetization free layers 6 and therefore output can be obtained depending on the relative angle between the magnetization direction of the first ferromagnetic sub-layers 6B and the direction of the injected spins. Magnetic flux entering in an X-direction turns the magnetization direction of each first ferromagnetic sub-layer 6B and therefore the magnitude of the magnetic flux can be detected by measuring the voltage between the first ferromagnetic sub-layer 6B and each channel layer 5. Furthermore, as shown in FIG. 6, a plurality of the magnetization free layers 6 are arranged, whereas the magnetization-fixed layer 7 functions as a spin injection source and is common to the magnetic sensors. Therefore, the magnitude and shape of an external magnetic field can be measured by comparing the voltages of the neighboring magnetization free layers 6 to each other.

In general, as the distance between the magnetization-fixed layer 7 and each magnetization free layer 6 is smaller, a spin accumulation magnetic sensor provides a higher output. Arranging a plurality of such spin accumulation magnetic sensors enables where fine magnetic particles are located, the number of the fine magnetic particles, and the size of the fine magnetic particles to be detected. For example, specific cells are modified with magnetic beads and are moved above such magnetic sensors as shown in FIG. 6. When the magnetic beads approach the magnetic sensors shown in FIG. 6, the magnetic sensors detect the magnetic flux from the magnetic beads. The number and size of the magnetic beads can be judged by analyzing signals detected by the magnetic sensors.

EXAMPLES

Example 1

The magnetic sensor 100a according to the first embodiment was manufactured by a method below. First, the lower magnetic shield layer 1 and the first insulating layer 3 were continuously formed on a substrate provided with a thermal silicon oxide film by a sputtering process in that order. Next, a portion of the first insulating layer 3 was ground by milling, followed by forming the first electrode 4 on the ground portion.

Next, a surface of the first insulating layer 3 and a surface of the first electrode 4 were polished by chemical mechanical polishing (CMP) so as to be planarized. Thereafter, the channel layer 5, the magnetization-fixed layer 7, and the antiferromagnetic layer 8 were continuously formed on the planarized surfaces in that order. The thickness of the channel layer 5 was 0.01 µm.

Furthermore, the channel layer 5 was processed by milling and chemical etching so as to have a strip shape with a longitudinal axis in an X-direction. Incidentally, the magnetization-fixed layer 7 was composed of the second ferromagnetic sub-layer 7B and the channel layer 5 and the second ferromagnetic sub-layer 7B were formed in that order. The second tunnel barrier sub-layer 7A was not formed. The channel layer 5 was made of Ag. Before the second ferromagnetic sub-layer 7B was formed, the channel layer 5, which was made of Ag, was surface-modified with Ar plasma. The second ferromagnetic sub-layer 7B was made of an alloy of cobalt and iron.

As the second section, the channel layer 5, the magnetization-fixed layer 7, and the antiferromagnetic layer 8 were ground by ion milling such that the magnetization-fixed layer 7 had a strip shape with a longitudinal axis in a Z-direction, followed by providing an insulating film on the antiferromagnetic layer 8. Thereafter, as the first section, the channel layer 5 was ground so as to take the form of the strip-shaped magnetization free layer 6, followed by forming the magnetization free layer 6 on the channel layer 5. In this operation, the thickness d1 of the first section of the channel layer 5 was reduced to 0.005 µm. The magnetization free layer 6 was prepared so as to extend 0.1 µm in the X-direction and 0.1 µm in the Z-direction. The magnetization-fixed layer 7 was prepared so as to extend 0.1 µm in the X-direction and 1 µm in the Z-direction. The distance of closest approach between the magnetization free layer 6 and the magnetization-fixed layer 7 in the X-direction was 1 µm. Incidentally, the magnetization free layer 6 was composed of the first ferromagnetic sub-layer 6B and the channel layer 5 and the first ferromagnetic sub-layer 6B were formed in that order. The first tunnel sub-layer 6A was not formed. The first ferromagnetic sub-layer 6B was made of an alloy of cobalt and iron. Before the first ferromagnetic sub-layer 6B was formed, the same material as that used to form the channel layer 5 was deposited by 0.002 µm, followed by forming the magnetization free layer 6 (first ferromagnetic sub-layer 6B).

Since the channel layer 5 was surface-modified with Ar plasma before the second ferromagnetic sub-layer 7B was formed thereon, the interface between the channel layer 5 and the magnetization-fixed layer 7 was irregular. However, since the channel layer 5 and the first ferromagnetic sub-layer 6B were continuously formed, the interface between the channel layer 5 and the magnetization free layer 6 was less irregular. Therefore, the areal resistance of the interface between the channel layer 5 and the magnetization free layer 6 was lower than the areal resistance of the interface between the channel layer 5 and the magnetization-fixed layer 7. In this stage, the thickness d1 of the first section of the channel layer 5 was 0.007 µm and the thickness d2 of the second section of the channel layer 5 was 0.01 µm.

A superfluous layer on the magnetization free layer 6 was ground and the upper first magnetic shield layer 11 was then formed. After an insulating layer on the antiferromagnetic layer 8 was ground and the second electrode 9 was then formed, the upper second magnetic shield layer 12 was formed. As described above, the magnetic sensor 100a was completed.

A current was applied to the magnetization-fixed layer 7 (second ferromagnetic sub-layer 7B) from the first electrode 4 through the channel layer 5 as shown in FIG. 1 and the voltage between the magnetization free layer 6 (first ferromagnetic sub-layer 6B) was measured. As a result, when a current of 5 mA was applied to the magnetization-fixed layer 7, the output was 6 µV. The noise defined as the amplitude of a signal with respect to an output waveform was 0.04 µV.

The resistance of the interface between the channel layer 5 and the magnetization free layer 6 or the magnetization-fixed layer 7 was measured by a three-terminal method. The resistance of the interface between the channel layer 5 and the magnetization free layer 6 was measured as follows: the upper first magnetic shield layer 11 and the upper second magnetic shield layer 12 were connected to a current source, a current was applied between the first ferromagnetic sub-layer 6B and the channel layer 5, a voltage-measuring system was connected to the upper first magnetic shield layer 11 and an end portion of the channel layer 5 that was overlaid with the magnetization free layer 6, and the resistance between the first ferromagnetic sub-layer 6B and the channel layer 5 was measured. The resistance of the interface between the channel layer 5 and the magnetization-fixed layer 7 was measured as follows: the lower magnetic shield layer 1 and the upper second magnetic shield layer 12 were connected to a current source, a current was applied between the second ferromagnetic sub-layer 7B and the channel layer 5, the voltage-measuring system was connected to the upper second magnetic shield layer 12 and the end portion of the channel layer 5 that was overlaid with the magnetization free layer 6, and the resistance between the second ferromagnetic sub-layer 7B and the channel layer 5 was measured. In this operation, the reason why the voltage-measuring system was connected to the end portion of the channel layer 5 that was overlaid with the magnetization free layer 6 was to mainly detect the resistance of the interface between the channel layer 5 and the magnetization free layer 6 or the magnetization-fixed layer 7 by avoiding measuring the voltage drop due to the current flowing through the channel layer 5. The voltage measured by this method was the voltage drop due to the sum of the resistance of the first ferromagnetic sub-layer 6B and the resistance of the interface between the magnetization free layer 6 and the channel layer 5 or the sum of the resistance of the second ferromagnetic sub-layer 7B and the resistance of the interface between the magnetization-fixed layer 7 and the channel layer 5. Since the resistance of the first ferromagnetic sub-layer 6B and the resistance of the second ferromagnetic sub-layer 7B were low, the resistance of the interface between the channel layer 5 and the magnetization free layer 6 or the magnetization-fixed layer 7 was mainly observed. The resistance of the interface between the magnetization free layer 6 and the channel layer 5 was 4.0Ω. The resistance of the interface between the magnetization-fixed layer 7 and the channel layer 5 was 1.0Ω. Since the area of the interface between the magnetization free layer 6 and the channel layer 5 was 0.01 µm² and the area of the interface between the magnetization-fixed layer 7 and the channel layer 5 was 0.1 µm², the areal resistance of the interface between the magnetization free layer 6 and the channel layer 5 was 0.04Ω·µm² and the areal resistance of the interface between the magnetization-fixed layer 7 and the channel layer 5 was 0.1Ω·µm².

Example 2

Figure 4:
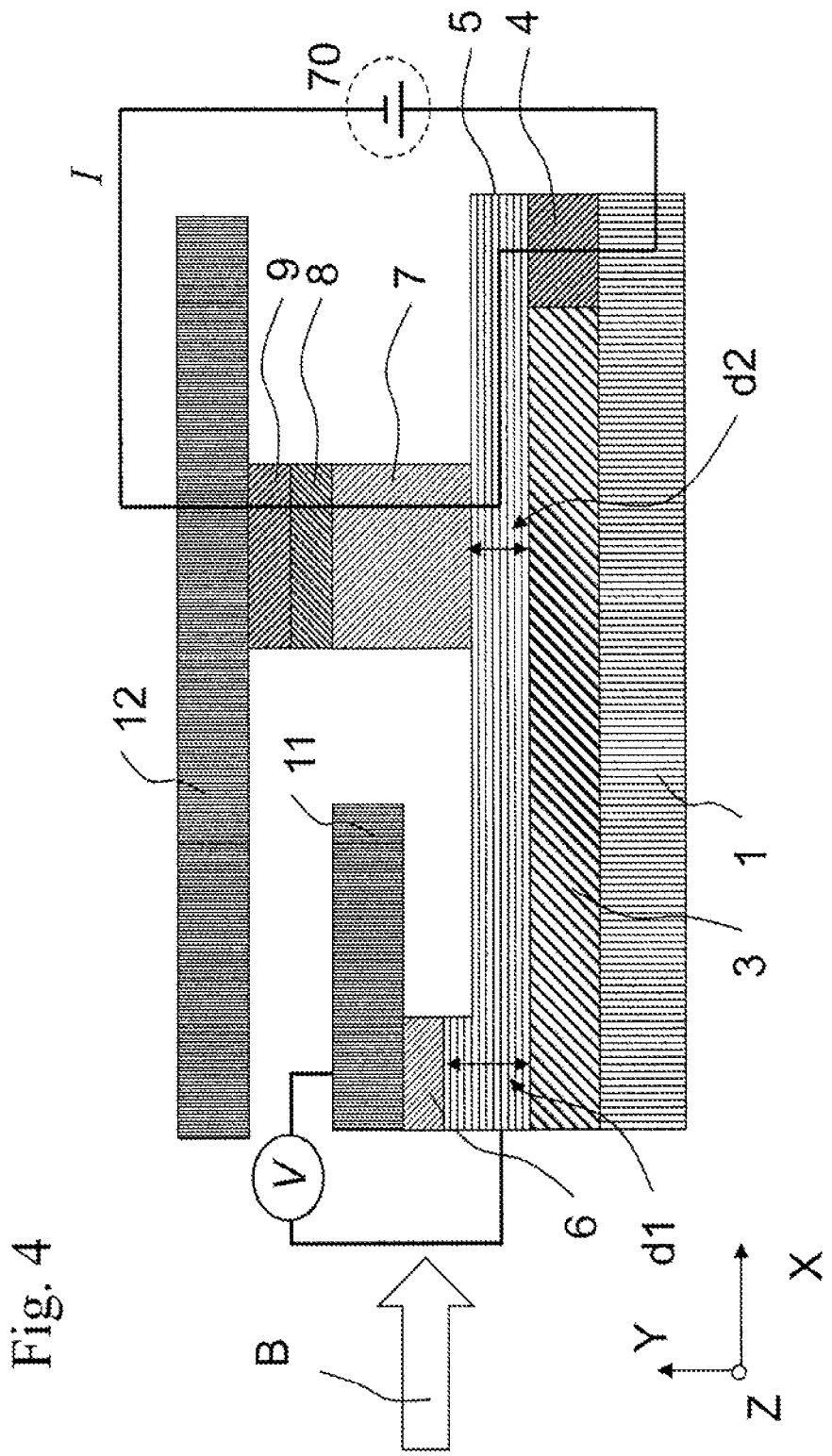
FIG. 4 is a schematic sectional view of a magnetic sensor different in configuration from the magnetic sensor shown in FIG. 1.

A magnetic sensor of Example 2 has a configuration shown in FIG. 4 and is different from the magnetic sensor 100a in that the thickness d2 of a second section of a channel layer 5 is less than the thickness d1 of a first section of the channel layer 5. The magnetic sensor of Example 2 was manufactured in substantially the same manner as that described in Example 1 except that the order of formation of a magnetization free layer 6 and a magnetization-fixed layer 7 was reversed.

A surface of a first insulating layer 3 and a surface of a first electrode 4 were polished by CMP so as to be planarized. Thereafter, the channel layer 5 and the magnetization free layer 6 were continuously formed on the planarized surfaces in that order. The thickness of the channel layer 5 was 0.01 µm. The magnetization free layer 6 and the channel layer 5 were processed by milling and chemical etching so as to have a strip shape with a longitudinal axis in an X-direction. Incidentally, the magnetization free layer 6 was composed of a first ferromagnetic sub-layer 6B and the channel layer 5 and the first ferromagnetic sub-layer 6B were formed in that order. A first tunnel barrier sub-layer 6A was not formed. The channel layer 5 was made of Ag. The first ferromagnetic sub-layer 6B was made of an alloy of cobalt and iron.

The channel layer 5 and the magnetization free layer 6 were ground by ion milling such that the magnetization free layer 6 had a rectangular shape, followed by forming an insulating film on the magnetization free layer 6. Thereafter, the channel layer 5 was ground so as to take the form of the magnetization-fixed layer 7 that was a strip shape with a longitudinal axis in a Z-direction, followed by forming the magnetization-fixed layer 7 on the channel layer 5. In this operation, the thickness d2 of the second section of the channel layer 5 was reduced to 0.007 µm. Before the magnetization-fixed layer 7 was formed, the channel layer 5 was surface-modified with Ar plasma. The magnetization free layer 6 was prepared so as to extend 0.1 µm in the X-direction and 0.1 µm in the Z-direction. The magnetization-fixed layer 7 was prepared so as to extend 0.1 µm in the X-direction and 1 µm in the Z-direction. The distance of closest approach between the magnetization free layer 6 and the magnetization-fixed layer 7 in the X-direction was 1 µm. Incidentally, the magnetization-fixed layer 7 was composed of a second ferromagnetic sub-layer 7B and the channel layer 5 and the second ferromagnetic sub-layer 7B were formed in that order. A second tunnel barrier sub-layer 7A was not formed. The second ferromagnetic sub-layer 7B was made of an alloy of cobalt and iron. Since the channel layer 5, on which the second ferromagnetic sub-layer 7B was formed, was surface-modified with Ar plasma, the interface between the channel layer 5 and the magnetization-fixed layer 7 was irregular. However, since the channel layer 5 and the first ferromagnetic sub-layer 6B were continuously formed, the interface between the channel layer 5 and the magnetization free layer 6 was less irregular. Therefore, the areal resistance of the interface between the channel layer 5 and the magnetization free layer 6 was lower than the areal resistance of the interface between the channel layer 5 and the magnetization-fixed layer 7. In this stage, the thickness d1 of the first section of the channel layer 5 was 0.01 µm and the thickness d2 of the second section of the channel layer 5 was 0.007 µm. When the thickness d2 of the second section of the channel layer 5 is less than the thickness d1 of the first section of the channel layer 5, a high output is obtained as compared to the case where the thickness d1 of the first section of the channel layer 5 is less than the thickness d2 of the second section of the channel layer 5.

An insulating layer on the magnetization free layer 6 was ground and an upper first magnetic shield layer 11 was formed. After an insulating layer on an antiferromagnetic layer 8 was ground and a second electrode 9 was then formed, an upper second magnetic shield layer 12 was formed. As described above, the magnetic sensor of Example 2 was completed.

The magnetic sensor of Example 2 was evaluated in the same manner as that described in Example 1. As a result, when a current of 5 mA was applied to the magnetization-fixed layer 7, the output was 8 µV. The noise defined as the amplitude of a signal with respect to an output waveform was 0.04 µV. The resistance of the interface between the magnetization free layer 6 and the channel layer 5 was 3.0Ω. The resistance of the interface between the magnetization-fixed layer 7 and the channel layer 5 was 1.0Ω. Since the area of the interface between the magnetization free layer 6 and the channel layer 5 was 0.01 µm² and the area of the interface between the magnetization-fixed layer 7 and the channel layer 5 was 0.1 µm², the areal resistance of the interface between the magnetization free layer 6 and the channel layer 5 was 0.03Ω·μm² and the areal resistance of the interface between the magnetization-fixed layer 7 and the channel layer 5 was 0.1Ω·μm².

Example 3

A magnetic sensor of Example 3 was manufactured in substantially the same manner as that described in Example 1. However, a channel layer 5 made of Ag was not surface-modified with Ar plasma, although surface modification was performed in Example 1. Unlike Example 1, in a magnetization-fixed layer 7, a second tunnel barrier sub-layer 7A was placed between the channel layer 5 and a second ferromagnetic sub-layer 7B and, in magnetization free layer 6, a first tunnel barrier sub-layer 6A was placed between the channel layer 5 and a first ferromagnetic sub-layer 6B.

The magnetization-fixed layer 7 was composed of the second tunnel barrier sub-layer 7A and the second ferromagnetic sub-layer 7B. The channel layer 5, the second tunnel barrier sub-layer 7A, and the second ferromagnetic sub-layer 7B were formed in that order. The channel layer 5 was made of Ag. The second tunnel barrier sub-layer 7A had a thickness of 2.2 nm and was made of MgO. The second ferromagnetic sub-layer 7B was made of an alloy of cobalt and iron.

The magnetization free layer 6 was composed of the first tunnel barrier sub-layer 6A and the first ferromagnetic sub-layer 6B. The channel layer 5, the first tunnel barrier sub-layer 6A, and the first ferromagnetic sub-layer 6B were formed in that order. The first tunnel barrier sub-layer 6A had a thickness of 0.8 nm and was made of MgO. The first ferromagnetic sub-layer 6B was made of an alloy of cobalt and iron.

The magnetic sensor of Example 3 was evaluated in the same manner as that described in Example 1. As a result, when a current of 5 mA was applied to the magnetization-fixed layer 7, the output was 30 V. The noise defined as the amplitude of a signal with respect to an output waveform was 0.5 μV. The resistance of the interface between the magnetization free layer 6 and the channel layer 5 was 10Ω. The resistance of the interface between the magnetization-fixed layer 7 and the channel layer 5 was 800Ω. Since the area of the interface between the magnetization free layer 6 and the channel layer 5 was 0.01 μm² and the area of the interface between the magnetization-fixed layer 7 and the channel layer 5 was 0.1 μm², the areal resistance of the interface between the magnetization free layer 6 and the channel layer 5 was 0.1Ω·μm² and the areal resistance of the interface between the magnetization-fixed layer 7 and the channel layer 5 was 80Ω·μm².

Example 4

A magnetic sensor of Example 4 was manufactured in substantially the same manner as that described in Example 2. However, a channel layer 5 made of Ag was not surface-modified with Ar plasma, although surface modification was performed in Example 2. Unlike Example 2, in a magnetization-fixed layer 7, a second tunnel barrier sub-layer 7A was placed between the channel layer 5 and a second ferromagnetic sub-layer 7B and, in magnetization free layer 6, a first tunnel barrier sub-layer 6A was placed between the channel layer 5 and a first ferromagnetic sub-layer 6B.

The magnetization free layer 6 was composed of the first tunnel barrier sub-layer 6A and the first ferromagnetic sub-layer 6B. The channel layer 5, the first tunnel barrier sub-layer 6A, and the first ferromagnetic sub-layer 6B were formed in that order. The channel layer 5 was made of Ag. The first tunnel barrier sub-layer 6A had a thickness of 0.8 nm and was made of MgO. The first ferromagnetic sub-layer 6B was made of an alloy of cobalt and iron.

The magnetization-fixed layer 7 was composed of the second tunnel barrier sub-layer 7A and the second ferromagnetic sub-layer 7B. The channel layer 5, the second tunnel barrier sub-layer 7A, and the second ferromagnetic sub-layer 7B were formed in that order. The second tunnel barrier sub-layer 7A had a thickness of 2.2 nm and was made of MgO. The second ferromagnetic sub-layer 7B was made of an alloy of cobalt and iron.

The magnetic sensor of Example 4 was evaluated in the same manner as that described in Example 1. As a result, when a current of 5 mA was applied to the magnetization-fixed layer 7, the output was 33 μV. The noise defined as the amplitude of a signal with respect to an output waveform was 0.5 μV. The resistance of the interface between the magnetization free layer 6 and the channel layer 5 was 8.0Ω. The resistance of the interface between the magnetization-fixed layer 7 and the channel layer 5 was 820Ω. Since the area of the interface between the magnetization free layer 6 and the channel layer 5 was 0.01 μm² and the area of the interface between the magnetization-fixed layer 7 and the channel layer 5 was 0.1 μm², the areal resistance of the interface between the magnetization free layer 6 and the channel layer 5 was 0.08Ω·μm² and the areal resistance of the interface between the magnetization-fixed layer 7 and the channel layer 5 was 82Ω·μm².

Comparative Example 1

In Comparative Example 1, a magnetic sensor was manufactured in substantially the same manner as that described in Examples 1 and 2. However, a magnetization-fixed layer 7 and a magnetization free layer 6 were formed by the same process. A channel layer 5 was formed so as to include a first section with a thickness of 0.007 μm and a second section with a thickness of 0.007 μm. First, a lower magnetic shield layer 1 and a first insulating layer 3 were continuously formed on a substrate provided with a thermal silicon oxide film by a sputtering process in that order. Next, a portion of the first insulating layer 3 was ground by milling, followed by forming a first electrode 4 on the ground portion.

Next, a surface of the first insulating layer 3 and a surface of the first electrode 4 were polished by CMP so as to be planarized. Thereafter, the channel layer 5, the magnetization free layer 6, the magnetization-fixed layer 7, and an antiferromagnetic layer 8 were continuously formed on the planarized surfaces in that order. The channel layer 5 had a thickness of 0.007 μm. In Comparative Example 1, the magnetization free layer 6 and the magnetization-fixed layer 7 were made from the same film and were formed in the form of a single film. Before the magnetization free layer 6 and the magnetization-fixed layer 7 were formed, the channel layer 5 was surface-modified with Ar plasma.

Furthermore, the channel layer 5 was processed by milling and chemical etching so as to have a strip shape with a longitudinal axis in an X-direction. Incidentally, the magnetization-fixed layer 7 was composed of a second ferromagnetic sub-layer 7B and the channel layer 5 and the second ferromagnetic sub-layer 7B were formed in that order. The magnetization free layer 6 was composed of a first ferromagnetic sub-layer 6B and the channel layer 5 and the first ferromagnetic sub-layer 6B were formed in that order. The channel layer 5 was made of Ag. The first ferromagnetic sub-layer 6B and the second ferromagnetic sub-layer 7B were made of an alloy of cobalt and iron.

The channel layer 5, the magnetization free layer 6, and the magnetization-fixed layer 7 were ground by ion milling such that the magnetization free layer 6 had a rectangular shape and the magnetization-fixed layer 7 had a strip shape with a longitudinal axis in a Z-direction, followed by forming an insulating film on the magnetization free layer 6 and the antiferromagnetic layer 8, which was placed on the magnetization-fixed layer 7. In this operation, the aspect ratio of the magnetization-fixed layer 7 was adjusted above the aspect ratio of the magnetization free layer 6. The magnetization free layer 6 was prepared so as to extend 0.1 µm in the X-direction and 0.1 µm in the Z-direction. The magnetization-fixed layer 7 was prepared so as to extend 0.1 µm in the X-direction and 1 µm in the Z-direction. The distance of closest approach between the magnetization free layer 6 and the magnetization-fixed layer 7 in the X-direction was 1 µm. Next, an insulating layer placed on the magnetization free layer 6 and the antiferromagnetic layer 8 were ground by ion milling. Thereafter, an upper first magnetic shield layer 11, a second electrode 9, and an upper second magnetic shield layer 12 were formed in the same manner as that described in Example 1.

The magnetic sensor was evaluated in the same manner as that described in Example 1. As a result, when a current of 5 mA was applied to the magnetization-fixed layer 7, the output was 4 µV. The noise defined as the amplitude of a signal with respect to an output waveform was 0.16 µV. The resistance of the interface between the magnetization free layer 6 and the channel layer 5 was 10Ω. The resistance of the interface between the magnetization-fixed layer 7 and the channel layer 5 was 1.0Ω. Since the area of the interface between the magnetization free layer 6 and the channel layer 5 was 0.01 µm$^2$ and the area of the interface between the magnetization-fixed layer 7 and the channel layer 5 was 0.1 µm$^2$, the areal resistance of the interface between the magnetization free layer 6 and the channel layer 5 was 0.1Ω·µm$^2$ and the areal resistance of the interface between the magnetization-fixed layer 7 and the channel layer 5 was 0.1Ω·µm$^2$.

Comparative Example 2

In Comparative Example 2, a magnetic sensor was manufactured in substantially the same manner as that described in Examples 3 and 4. However, a magnetization-fixed layer 7 and a magnetization free layer 6 were formed by the same process. A channel layer 5 was formed so as to include a first section with a thickness of 0.007 µm and a second section with a thickness of 0.007 µm. First, a lower magnetic shield layer 1 and a first insulating layer 3 were continuously formed on a substrate provided with a thermal silicon oxide film by a sputtering process in that order. Next, a portion of the first insulating layer 3 was ground by milling, followed by forming a first electrode 4 on the ground portion.

Next, a surface of the first insulating layer 3 and a surface of the first electrode 4 were polished by CMP so as to be planarized. Thereafter, the channel layer 5, the magnetization free layer 6, the magnetization-fixed layer 7, and an antiferromagnetic layer 8 were continuously formed on the planarized surfaces in that order. The channel layer 5 had a thickness of 0.007 µm. In Comparative Example 2, the magnetization free layer 6 and the magnetization-fixed layer 7 were made from the same film and were formed in the form of a single film.

Furthermore, the channel layer 5 was processed by milling and chemical etching so as to have a strip shape with a longitudinal axis in an X-direction. Incidentally, the magnetization-fixed layer 7 was composed of a second tunnel barrier sub-layer 7A and a second ferromagnetic sub-layer 7B and the channel layer 5, the second tunnel barrier sub-layer 7A, and the second ferromagnetic sub-layer 7B were formed in that order. The magnetization free layer 6 was composed of a first tunnel barrier sub-layer 6A and a first ferromagnetic sub-layer 6B and the channel layer 5, the first tunnel barrier sub-layer 6A, and the first ferromagnetic sub-layer 6B were formed in that order. The channel layer 5 was made of Ag. The first tunnel barrier sub-layer 6A and the second tunnel barrier sub-layer 7A had a thickness of 2.2 nm and were made of MgO. The first ferromagnetic sub-layer 6B and the second ferromagnetic sub-layer 7B were made of an alloy of cobalt and iron.

The channel layer 5, the magnetization free layer 6, and the magnetization-fixed layer 7 were ground by ion milling such that the magnetization free layer 6 had a rectangular shape and the magnetization-fixed layer 7 had a strip shape with a longitudinal axis in a Z-direction, followed by forming an insulating film on the magnetization free layer 6 and the antiferromagnetic layer 8, which was placed on the magnetization-fixed layer 7. In this operation, the aspect ratio of the magnetization-fixed layer 7 was adjusted above the aspect ratio of the magnetization free layer 6. The magnetization free layer 6 was prepared so as to extend 0.1 µm in the X-direction and 0.1 µm in the Z-direction. The magnetization-fixed layer 7 was prepared so as to extend 0.1 µm in the X-direction and 1 µm in the Z-direction. The distance of closest approach between the magnetization free layer 6 and the magnetization-fixed layer 7 in the X-direction was 1 µm. Next, an insulating layer placed on the magnetization free layer 6 and the antiferromagnetic layer 8 were ground by ion milling. Thereafter, an upper first magnetic shield layer 11, a second electrode 9, and an upper second magnetic shield layer 12 were formed in the same manner as that described in Example 1.

The magnetic sensor was evaluated in the same manner as that described in Example 1. As a result, when a current of 5 mA was applied to the magnetization-fixed layer 7, the output was 29 µV. The noise defined as the amplitude of a signal with respect to an output waveform was 4 µV. The resistance of the interface between the magnetization free layer 6 and the channel layer 5 was 7,500Ω. The resistance of the interface between the magnetization-fixed layer 7 and the channel layer 5 was 750Ω. Since the area of the interface between the magnetization free layer 6 and the channel layer 5 was 0.01 µm$^2$ and the area of the interface between the magnetization-fixed layer 7 and the channel layer 5 was 0.1 µm$^2$, the areal resistance of the interface between the magnetization free layer 6 and the channel layer 5 was 75Ω·µm$^2$ and the areal resistance of the interface between the magnetization-fixed layer 7 and the channel layer 5 was 75Ω·µm$^2$.

Results obtained in Examples 1 to 4 and Comparative Examples 1 and 2 are summarized in Table. Comparing the examples and the comparative examples to each other depending on whether a tunnel barrier sub-layer is present shows that the noise level of each example is a fraction of the noise level of a corresponding one of the comparative examples, although the outputs thereof are substantially equal. Thus, a high S/N ratio can be obtained in such a manner that the areal resistance of the interface between a channel layer 5 and a magnetization free layer 6 is adjusted below the areal resistance of the interface between the channel layer 5 and a magnetization-fixed layer 7.

TABLE

| | Resistance of interface between channel layer and magnetization free layer (Ω) | Resistance of interface between channel layer and magnetization-fixed layer (Ω) | Areal resistance of interface between channel layer and magnetization-free layer (Ω·μm$^2$) | Areal resistance of interface between channel layer and magnetization-fixed layer (Ω·μm$^2$) | Output (μV) | Noise (μV) | S/N ratio |
|---|---|---|---|---|---|---|---|
| Example 1 | 4.0 | 1.0 | 0.04 | 0.1 | 6 | 0.04 | 150 |
| Example 2 | 3.0 | 1.0 | 0.03 | 0.1 | 8 | 0.04 | 200 |
| Example 3 | 10 | 800 | 0.1 | 80 | 30 | 0.5 | 60 |
| Example 4 | 8.0 | 820 | 0.08 | 82 | 33 | 0.5 | 66 |
| Comparative Example 1 | 10 | 1.0 | 0.1 | 0.1 | 4 | 0.16 | 25 |
| Comparative Example 2 | 7,500 | 750 | 75 | 75 | 29 | 4 | 7.25 |

Examples 1 and 2 are those in which the resistance of the interface between the channel layer 5 and the magnetization free layer 6 is higher than the resistance of the interface between the channel layer 5 and the magnetization-fixed layer 7. Examples 3 and 4 are those in which the resistance of the interface between the channel layer 5 and the magnetization free layer 6 is lower than the resistance of the interface between the channel layer 5 and the magnetization-fixed layer 7. In every example, a high S/N ratio is obtained in such a manner that the areal resistance of the interface between the channel layer 5 and the magnetization free layer 6 is adjusted below the areal resistance of the interface between the channel layer 5 and the magnetization-fixed layer 7. Even in the case where the resistance of the interface between the channel layer 5 and the magnetization free layer 6 is equal to the resistance of the interface between the channel layer 5 and the magnetization-fixed layer 7, a high S/N ratio is obtained in such a manner that the areal resistance of the interface between the channel layer 5 and the magnetization free layer 6 is adjusted below the areal resistance of the interface between the channel layer 5 and the magnetization-fixed layer 7.

What is claimed is:

1. A magnetic sensor comprising:
   a channel layer;
   a magnetization free layer placed on a first section of the channel layer; and
   a magnetization-fixed layer placed on a second section of the channel layer,
   wherein an interface between the channel layer and the magnetization free layer has an areal resistance that is lower than an areal resistance of an interface between the channel layer and the magnetization-fixed layer, and
   the magnetization free layer includes a first ferromagnetic sub-layer and a first tunnel barrier sub-layer placed between the first ferromagnetic sub-layer and the channel layer, the magnetization-fixed layer includes a second ferromagnetic sub-layer and a second tunnel barrier sublayer placed between the second ferromagnetic sub-layer and the channel layer, and the first tunnel barrier sub-layer has a thickness that is less than a thickness of the second tunnel barrier sub-layer.

2. The magnetic sensor according to claim 1, wherein the first section of the channel layer has a thickness that is less than a thickness of the second section of the channel layer.

3. The magnetic sensor according to claim 1, wherein the second section of the channel layer has a thickness that is less than a thickness of the first section of the channel layer.

4. A magnetic head comprising:
   a reading head section including the magnetic sensor according to claim 1; and
   a recording head section for writing.

5. A biomagnetic sensor comprising a plurality of magnetic sensors, each magnetic sensor comprising:
   a channel layer;
   a magnetization free layer placed on a first section of the channel layer; and
   a magnetization-fixed layer placed on a second section of the channel layer,
   wherein an interface between the channel layer and the magnetization free layer has an areal resistance that is lower than an areal resistance of an interface between the channel and the magnetization-fixed layer.

6. A magnetic sensor comprising:
   a channel layer;
   a magnetization free layer placed on a first section of the channel layer; and
   a magnetization-fixed layer placed on a second section of the channel layer,
   wherein an interface between the channel layer and the magnetization free layer has an areal resistance that is lower than an areal resistance of an interface between the channel layer and the magnetization-fixed layer, and
   the first section of the channel layer has a thickness that is less than a thickness of the second section of the channel layer.

7. The magnetic sensor according to claim 6, wherein the magnetization free layer includes a first ferromagnetic sub-layer and a first tunnel barrier sub-layer placed between the first ferromagnetic sub-layer and the channel layer, the magnetization-fixed layer includes a second ferromagnetic sub-layer and a second tunnel barrier sub-layer placed between the second ferromagnetic sub-layer and the channel layer, and the first tunnel barrier sub-layer has a thickness that is less than a thickness of the second tunnel barrier sub-layer.

8. A magnetic head comprising:
   a reading head section including the magnetic sensor according to claim 6, and
   a recording head section for writing.

9. A magnetic sensor comprising:
   a channel layer;
   a magnetization free layer placed on a first section of the channel layer; and
   a magnetization-fixed layer placed on a second section of the channel layer, wherein an interface between the channel layer and the magnetization free layer has an areal resistance that is lower than an areal resistance of an interface between the channel layer and the magnetization-fixed layer, and the second section of the channel layer has a thickness that is less than a thickness of the first section of the channel layer.

10. The magnetic sensor according to claim 9, wherein the magnetization free layer includes a first ferromagnetic sub-layer and a first tunnel barrier sub-layer placed between the first ferromagnetic sub-layer and the channel layer, the magnetization-fixed layer includes a second ferromagnetic sub-layer and a second tunnel barrier sub-layer placed between the second ferromagnetic sub-layer and the channel layer, and the first tunnel barrier sub-layer has a thickness that is less than a thickness of the second tunnel barrier sub-layer.

11. A magnetic head comprising:
a reading head section including the magnetic sensor according to claim 9, and
a recording head section for writing.

* * * * *